United States Patent [19]

Ernst et al.

[11] Patent Number: 5,082,959
[45] Date of Patent: * Jan. 21, 1992

[54] PROCESS FOR PREPARING SILYLATED AROMATIC ACIDS

[75] Inventors: Andreas B. Ernst, Glen Ellyn; Howard B. Yokelson, Aurora; Robert K. Gipe, Wheaton, all of Ill.

[73] Assignee: Amoco Corporation, Chicago, Ill.

[*] Notice: The portion of the term of this patent subsequent to Jul. 10, 2007 has been disclaimed.

[21] Appl. No.: 578,892

[22] Filed: Sep. 6, 1990

[51] Int. Cl.$^5$ .............................................. C07F 7/08
[52] U.S. Cl. .................................. 556/438; 556/439; 556/430
[58] Field of Search .................. 556/438, 439, 430

[56] References Cited

U.S. PATENT DOCUMENTS 4,940,810  7/1990  Yokelson et al. ................... 556/438

Primary Examiner—Paul F. Shaver
Attorney, Agent, or Firm—Gunar J. Blumberg; William H. Magidson; Ralph C. Medhurst

[57] ABSTRACT

An improved process is disclosed for preparation of silicon-containing aromatic polyacids by liquid phase oxidation of a silyl compound in the presence of oxygen and a catalyst comprising cobalt-manganese-bromine. 2-Trimethylsilyl-p-xylene is oxidized to 2-trimethylsilyl-terephthalic acid; 5-trimethylsilyl-m-xylene is oxidized to 5-trimethylsilyl-isophthalic acid, 2,5-bis (trimethylsilyl)-p-xylene is oxidized to 2,5-bis (trimethylsilyl)-terephthalic acid; 5-trimethylsilyl-pseudocumene is oxidized to 1,2,4-tricarboxy-5-trimethylsilyl benzene; and 1,3-bis-(p-tolyl)-tetramethyl-disiloxane is oxidized to 1,3-bis(p-carboxyphenyl)-tetramethyl-disiloxane.

12 Claims, No Drawings

PROCESS FOR PREPARING SILYLATED AROMATIC ACIDS

FIELD OF THE INVENTION

This invention relates to a process for preparation of silicon-containing aromatic polyacids by a liquid phase oxidation of a mono- or poly(mono- or polyalkyl-, aryl, oxo-, siloxy, or silyl-substituted) silyl substituted mono- or polyalkyl-substituted aryl compound comprising an alkyl-substituted or aryl-substituted aryl mono- or polyalkyl silyl wherein alkyl groups or aryl groups in the alkyl-substituted or aryl-substituted mono- or polyalkyl silyl contain from 1 to 100 carbon atoms, the number of alkyl groups on the alkyl-substituted aryl mono- or polyalkyl silyl are from 1 to 4, the number of groups in the aryl-substituted aryl-, mono- or polyalkyl silyl are from 1 to 4, and the alkyl groups on the silicon atom contain from 1 to 20 carbon atoms. More particularly, the field of this invention relates to the preparation of 2-trimethylsilyl-terephthalic acid, 5-trimethylsilyl-isophthalic acid, 2-trimethylsilyl-phthalic acid, 1-trimethylsilyl-2,6-dicarboxynaphthalene, 1,2,4-tricarboxy-5-trimethylsilyl benzene, 1-trimethylsilyl-2,6-dicarboxynaphthalene, and 2,5-bis(trimethylsilyl) terephthalic acid.

BACKGROUND OF THE INVENTION

Organosilicon polymers, as a class of engineering thermoplastics, have good heat resistance and excellent mechanical properties. A precursor for polyesters, polyamides, polyimides or polyamide-imides having organosilicon components is a polyfunctional molecule having an organosilicon moiety, preferably of a polycarboxylic character which can be reacted readily with an alcohol or an amine, etc., to produce a polyester, polyamide, polyimide, or polyamide-imide, etc., of suitable chain length. Such precursors include silicon-containing aromatic polyacids such as 2-trimethylsilyl-terephthalic acid and 5-trimethylsilyl-isophthalic acid, both of which have been described in the proir art.

Despite the preparation of 2-trimethylsilyl-terephthalic acid and 5-trimethylsilyl-isophthalic acid, as noted above, prior investigators have not extensively pursued the application of these materials in polymers. Preparation of these materials by procedures described in the prior art typically resulted in products contaminated with oxidation by-products which required recrystallization steps to remove. For example, as is taught in Helv. Chim. Acta 51, 553-6 (1968) and Helv. Chim. 54, 117-35 (1971), stoichiometric oxidations of 2-trimethylsilyl-p-xylene and 5-trimethylsilyl-m-xylene with potassium permanganate in aqueous pyridene yielded 92% and 91% of 2-methylsilyl-terephthalic acid and 5-trimethylsilyl-isophthalic acid respectively. However, the reaction products contain toluic acid partial oxidation products and manganese dioxide which must be removed before further use of the products can be attempted. In addition, the use of highly corrosive potassium permanganate requires process equipment able to withstand such corrosive action and prevent added contamination of the product from corrosive attack of the process equipment.

Surprisingly, it has been found that silicon-containing acids such as 2-trimethylsilyl-terephthalic acid and 5-trimethylsilyl-isophthalic acid can be prepared by a catalytic reaction using a cobalt-manganese-bromine catalyst in the presence of oxygen as the oxidant. The instant invented process offers severl adavantages over prior art processes in (1) that the reaction is catalytic rather than stoichiometric, thus offering a raw material advantage, (2) molecular oxygen is the oxidant rather than an oxidizer such as potassium permanganate with its concurrent production of by-products by reduction of the oxidizing agent, and (3) the by-product of the catalytic oxidative process is water which is easier to remove from the catalytic reaction products than the by-products of the stoichiometric oxidation process.

SUMMARY OF THE INVENTION

A liquid phase process is disclosed for the catalytic oxidation of silylated alkyl-substituted aromatic compounds with molecular oxygen in a solvent in the presence of a cobalt-manganese-bromine catalyst at an elevated temperature and pressure to prepare silylated aromatic acids. The silylated aromatic acids are useful as precursors for polyesters, polyamides, polyimides, and polyamide-imides.

DETAILS OF THE INVENTION

The instant invented process for preparation of silicon-containing aromatic polyacids is applicable to the liquid phase oxidation of any mono- or poly(mono- or polyalkyl-, aryl, oxo-, siloxy, or silyl-substituted) silyl substituted mono- or polyalkyl-substituted aryl compound comprising an alkyl-substituted or aryl-substituted aryl mono- or polyalkyl silyl wherein the alkyl groups or aryl groups contain from 1 to 100 carbon atoms, the number of alkyl groups on the alkyl-substituted aryl or polyalky silyl are from 1 to 4, the number of aryl groups in the aryl-substituted aryl mono- or polyalkyl silyl are from 1 to 4 and the alkyl groups on the silicon atom contain from 1 to 20 carbon atoms. In preferred embodiments of this invention, 2-trimethylsilyl-terephthalic acid is prepared from 2-trimethylsiyl-p-xylene, and 5-trimethylsilyl-isophthalic acid is prepared from 5-trimethylsilyl-m-xylene. 1,2,4-Tricarboxy-5-trimethylsilyl-benzene can be prepared from 5-trimethylsilyl-pseudocumene. Other silicon-containing aromatic polyacids which can be prepared by the invented process from suitable silyl substituted aryl compounds include 1-trimethylsilyl-2,6-dicarboxynaphthalene, 3,6-bis-trimethylsilyl-pyromellitic anhydride; 3-trimethylsilyl-pyromellitic dianhydride; 4,4'-oxy-bis[2,6-di(trimethylsilyl)benzoic acid]; 4,4'-oxy-bis(2-trimethylsilyl-benzoic acid); 2,2-di[(3,5-di-trimethylsilyl)-4-carboxyphenyl]propane; 2,2'di-(4-carboxy-3-trimethylsilyphenyl)propane; 4,4'-oxy-bis-(5-trimethylsilyl-phthalic anhydride); 4,4'-isopropylidene-bis(5-trimethylsilyl-phthalic anhydride); 4,4'-sulfonyl-bis-(2-trimethylsilyl-benzoic acid); 4,4'-sulfonyl-bis[2,6-di(trimethylsilyl) benzoic acid]; 4,4'-sulfonyl-bis-(5-trimethylsilyl-pthalic anhydride); 3,3',5,5'-tetrakis-(trimethylsilyl)-4,4'-dicarboxybiphenyl; 3,3'-bis-(trimethylsilyl)-4,4'-dicarboxybiphenyl; and 4,4'-bis-(5-trimethylsilyl-phthalic anhydride).

Suitable solvents for use in the instant invented process include any aliphatic $C_2$-$C_6$ monocarboxylic acid such as acetic acid, propionic acid, n-butyric acid, isobutyric acid, n-valeric acid, trimethylacetic and caproic acid and mixtures thereof. Preferably, the solvent is glacial acetic acid. The solvent can comprise a mixture of glacial acetic acid and acetic anhydride. Hydrolysis of the Si-C bond can occur in the presence of water. In the oxidation reactor slurry, the solvent preferably comprises less than 0.5 wt. % of water.

Since water is produced by the oxidation reaction, rate of production of water at a steady rate is controlled by the feed stream water concentration and the rates of withdraw of condensate and vapor from reactors and crystallizers, where the withdrawn material is dehydrated and then recycled. Low water concentration in the reaction increases production of the silylated acid. Reaction water concentration below 1 wt. % is preferable, more preferably below 0.5 wt. %.

When reactor slurry by-product concentration has exceeded a critical concentration because of changes in process parameters, by-product concentration can be adjusted by adjusting the reactor oxygen partial pressure. Rate of feed and pressure of an oxygen-containing gas controls oxygen partial pressure in the reaction mixture.

The source of molecular oxygen employed in a continous method of this invention can vary in molecular oxygen content from that of air to oxygen gas. Air is the preferred source of molecular oxygen. In order to avoid the formation of explosive mixtures in a continuous method, the oxygen-containing gas fed to the reactor should provide an exhaust gas-vapor mixture containing from 0.5 to 8 volume percent oxygen (measured on a solvent-free basis). For example, when each alkyl substituent on the aromatic ring of the alkyl aryl silyl is a methyl group, a feed rate of the amount of from 1.5 to 2.8 moles per methyl group will provide such 0.5 to 8 volume percent of oxygen (measured on a solvent-free basis) in the gas-vapor mixture in the condenser. Accordingly, reactor vent oxygen as volume percent of dry off gas can be in the range of from about 1 to about 6, preferably about 4.0 vol. % of vent gas on a dry basis.

The catalyst employed in the method of this invention comprises cobalt, manganese and bromine components, and can additionally comprise accelerators known in the art. The weight ratio of cobalt (calculated as elemental cobalt) in the cobalt component of the catalyst to the alkyl-substituted diaryldialkylsilyl in the liquid phase oxidation of the method of this invention is in the range of from about 0.2 to about 100 milligram atoms (mga) per gram mole of the alkyl-substituted diaryldialkylsilyl. The weight ratio of manganese (calculated as elemental manganese) in the manganese component of the catalyst to cobalt (calculated as elemental cobalt) in the cobalt component of the catalyst in the liquid phase oxidation of the method of this invention is in the range of from about 0.2 to about 10 mga per mga of cobalt. The weight ratio of bromine (calculated as elemental bromine) in the bromine component of the catalyst to total cobalt and manganese (calculated as elemental cobalt and elemental manganese) in the cobalt and manganese components of the catalyst in the liquid phase oxidation of the method of this invention is in range of from about 0.25 to about 1.2 mga per mga of total cobalt and manganese.

When reactor slurry by-product concentration has exceeded its critical concentration because of changes in process parameters, by-product concentration can be adjusted by adjusting the reactor solvent mole ratio of bromine to cobalt plus manganese.

Each of the cobalt, manganese and bromine components can be provided in any of the known ionic or combined forms that provide soluble forms of cobalt, manganese and bromine in the solvent in the reactor. For example, when the solvent is an acetic acid medium, cobalt and/or manganese, acetate tetrahydrate, and hydrogen bromide can be employed. The 0.25 to 1.2 bromine-to-total cobalt and manganese milligram atom ratio is provided by a suitable source of bromine. Bromine sources include elemental bromine ($Br_2$), ionic bromide (for example, NaBr, KBr, $NH_4Br$, etc.), or organic bromides which are known to provide bromide ions at the operating temperature of the oxidation (e.g., bromobenzenes, benzylbromide, mono-and dibromoacetic acid, bromoacetyl bromide, tetrabromoethane, ethylenedibromide, etc.). The total bromine in molecular bromine and ionic bromide is used to satisfy the bromine to metal atom ratio of 0.25 to 1.2. The bromide ion released from the organic bromides at the oxidation operating conditions can be readily determined by known analytical means. Tetrabromoethane, for example, at operating temperatures of about 340° F. (170° C.) to about 440° F. (225° C.) has been found to yield about 3 effective gram atoms of bromine per gram mole.

NaBr is preferred as a source of bromine. Hydrolysis of the Si-C bond can occur in the presence of water produced by the reaction or as a component of a reactant if such is used, such as hydrobromic acid.

The invented process can be in batch, semi-continuous or continuous method. A continuous method is preferred. Since the reaction produces water as a by-product, the increasing concentration of water with time that occurs in a batch reaction can cause the hydrolysis of the Si-C bond with increased formation of by-products such as toluic acid or terephthalic acid, or with corresponding loss of product yield.

In the continuous method of operation, the siloxy, oxidation feed comprising a mono- or poly(mono- or polyalkyl- aryl-, oxo-, siloxy, or silyl-substituted) silyl-substituted mono- or polyalkyl-substituted aryl compound, hereinafter referred to as silyl reactant, a source of oxygen, preferably air, a solvent, preferably glacial acetic acid or a mixture of glacial acetic acid and acetic anhydride, and catalyst are fed to the reaction zone at a rate such that preferred per pass oxidations are attained to prepare the desired carboxyphenyl silicon-containing aromatic polyacid compound. Depending upon equipment limitations, volumetric space velocity of the feed will determine contact time in the reaction zone and rate of production of water by the reaction.

Concentration of the silyl reactant relative to the solvent has been found to be preferably in the range of from about 1:12 to about 1:5, ratio of the silyl reactant to the solvent based upon weight.

From the exit end of the reaction zone in a continuous process, there is withdrawn an effluent comprising the oxidized product, by-product oxygenated silyl compounds, inert gas or gases, unreacted feed components, oxygen and water vapor. The effluent is passed to a separation zone in which the reaction products are separated and desired product substantially recovered. The remaining effluent after removal of the water can be returned to the reaction zone.

In an embodiment of the process of this invention, 2-trimethylsilyl-p-xylene is oxidized to 2-trimethylsilyl-terephthalic acid in the presence of a cobalt-manganese bromine catalyst in a solute comprising glacial acetic acid at a temperature within the range of from about 120° C. (250° F.) to about 260° C. (500° F.). Below 100° C., virtually no reaction occurs. Above about 260° C., the 2-trimethylsilyl-terephthalic acid is unstable with consequent decomposition and loss of product. Preferably, reaction temperature is in the range of from about 145° C. (293° F.) to about 165° C. (329° F.). Reaction pressure is in the range of from about 50 psig to about 750 psig, preferably from about 300 psig to about 600 psig. At pressures below 50 psig, virtually no reaction occurs. Pressures above 750 psig require high pressure process equipment with attendant economic costs.

In operation, the minimum pressure at which the reactor is maintained is that pressure which will maintain a substantial liquid phase of the silyl reactant and at least 70 percent of the solvent. The silyl reactant and solvent not in the liquid phase because of vaporization can be removed from the reactor as vapor-gas mixture, condensed and returned to the reactor. When the solvent is an acetic acid mixture, suitable reaction gauge pressure is in the range of from about 150 psig to about 600 psig, and typically is in the range of from about 250 psig to about 550 psig. The temperature range within the reactor is generally from about 120° C. (250° F.) to about 260° C. (500° F.), preferably from about 150° C. (300° F.), to about 165° C. (329° F.).

The instant invention comprises a batch, semi-continuous or continuous liquid phase process in a suitable reactor for the production of silylated aromatic acids, wherein the feedstream contains a silyl reactant comprising a silylated alkylated aromatic, by oxidation of said silylated alkylated aromatic in the presence of a cobalt-manganese-bromine catalyst which process comprises: a) preparing a reaction mixture containing an aliphatic $C_2$-$C_6$ monocarboxylic acid and said silyl reactant wherein water concentration is less than about 1.0 wt. %, preferably less than about 0.5 wt. %, wherein mole ratio of bromine to cobalt plus manganese of said catalyst is in the range of from about 0.35 to about 0.75; b) treating the reaction mixture with an oxygen-containing gas wherein vent oxygen in volume percent is from 0.5 to 8 volume % (measured on a solvent-free basis) to cause oxidation of the said silylated alkylated aromatic to silylated aromatic acids as product at a reaction temperature and at a reaction pressure to maintain the aqueous mixture in liquid phase; c) recovering said silylated aromatic acids as product from said reaction mixture wherein presence of reactor slurry by-product concentration is less than or no greater than a critical concentration determined principally by the reactor solvent mole ratio of bromine to cobalt plus manganese concentration at a temperature within the range of from about 140° C. (284° F.) to about 165° C. (329° F.).

In summary, the instant invention comprises a process for preparation of silicon-containing aromatic polyacids by liquid phase oxidation of a feedstock comprising a silyl reactant consisting essentially of a mono- or poly(mono- or polyalkyl-, aryl, oxo-, siloxy, or silyl-substituted) silyl substituted mono- or polyalkyl-substituted aryl compound hereinafter referred to as silyl reactant, wherein alkyl groups containing 1 to 20 carbon atoms in the alkyl-substituted aryl group number from 1 to 4, and the number of carbon atoms is from 1 to 20 in the alkyl groups attached to the silicon of the silyl group, which process comprises; a) introducing into a suitable reactor a feedstock comprising said silyl reactant in a solvent comprising an aliphatic $C_2$ to $C_6$ monocarboxylic acid; b) oxidizing said feedstock in the presence of a catalyst comprising cobalt-manganese-bromine with an oxygen-containing gas wherein the weight ratio of cobalt (calculated as elemental cobalt) to the said silyl reactant is in the range of from about 0.2 to about 100 milligram atoms (mga) per gram mole of said silyl reactant, weight ratio of manganese (calculated as elemental manganese) to the cobalt of said catalyst is in the range of from about 0.2 to 100 milligram atoms (mga) per mga of cobalt, and weight ratio of bromine in said catalyst (calculated as elemental bromine) to cobalt and manganese (calculated as elemental cobalt and manganese) is in the range of from about 0.25 to about 1.2 mga per mga of total cobalt and manganese, wherein said feedstock is present in a weight ratio to said aliphatic $C_2$ to $C_6$ monocarboxylic acid wherein the ratio of said feedstock to said acid is in the range of from about 1:10 to about 1:5 at a temperature within the range of from about 120° C. (250° F.) to about 260° C. (500° F.) and at a reaction pressure within the range of from about 50 psig to about 750 psig; and c) recovering a silicon-containing aromatic polyacid wherein said polyacid comprises a silylated aromatic acid.

In more detail, the instant invention comprises a process wherein said feedstock comprising said silyl reactant is selected from the group consisting of 2-trimethylsilyl-p-xylene, 5-trimethylsilyl-m-xylene, 2,5-bis(trimethylsilyl)-p-xylene, 1,2,4-trimethyl-5-trimethylsilyl-benzene, and 1,3-bis-(p-tolyl)-tetramethyl disiloxane. The said feedstock can comprise 2-trimethylsilyl-p-xylene, said $C_2$ to $C_6$ monocarboxylic acid is acetic acid, and said silicon-containing aromatic polyacid comprises 2-trimethylsilyl-terephthalic acid.

The said feedstock can comprise 5-trimethylsilyl-m-xylene, said $C_2$ to $C_6$ monocarboxylic acid is acetic acid, and said silicon-containing aromatic polyacid comprises 5-trimethylsilylisophthalic acid.

Similarly, the feedstock can comprise 2,5-bis(trimethylsilyl)-p-xylene and the silicon-containing aromatic polyacid comprises 2,5-bis(trimethylsilyl) terephthalic acid. Also, the feedstock can comprise 1,2,4-trimethyl-5-trimethylsilyl-benzene and the silicon-containing polyacid is 1,2,4-tricarboxy-5-trimethylsilyl-benzene. And, the feedstock can comprise 1,3-bis-(p-tolyl) tetramethyl-disiloxane and the silicon-containing polyacid is 1,3-bis-(p-carboxyphenyl)-tetramethyl-disiloxane. The feedstock can comprise 1-trimethylsilyl-2,6-dimethyl-naphthalene and the silicon-containing polyacid is 4-trimethylsilyl-2,6-dicarboxynaphthalene.

In one embodiment, the said oxygen-containing gas is air and said process is a continuous process wherein said oxygen-containing gas fed to said reactor provides an exhaust gas-vapor mixture containing from 0.5 to 8 volume percent oxygen, measured on a solvent-free basis.

In further detail, in an embodiment of the continuous method of the instant invention, the feedstock is selected from the group consisting of 2-trimethylsilyl-p-xylene, 5-trimethylsilyl-m-xylene, 2,5-bis(trimethylsilyl)-p-xylene, 1,2,4-trimethyl-5-trimethylsilylbenzene, 1,3-bis-(p-tolyl)-tetramethyl disiloxane, and 1-trimethylsilyl-2,6-dimethylnaphthalene, the $C_2$ to $C_6$ monocarboxylic acid is acetic acid, the mole ratio of manganese to cobalt is in the range of from about 0.2 to about 10.0, mole ratio of bromine to total cobalt plus manganese is about 0.2 to about 1.2, weight ratio of cobalt to said acetic acid, as glacial acetic acid, is in the range of from about 250 ppm to about 750 ppm, water content of the reaction mixture is from about 0.5 wt. % to about 2.0 wt. %, reaction temperature is in the range of from about 140° C. to about 165° C., reaction pressure is within the range of from about 200 psig to about 550 psig, and residence time is from about 30 minutes to about 6 hours.

The following examples illustrate the process of the invention but are not to be considered as limiting the scope of the invention.

EXAMPLE I

The following procedure illustrates the preparation of 2-trimethylsilyl-p-xylene which was used as the feed material to prepare 2-trimethylsilyl-terephthalic acid for use in Example IV. The silylxylene was prepared according to standard procedures for the preparation of these types of materials. A 2 L three-necked, round-bottomed flask equipped with a pressure equalizing addition funnel, overhead stirrer, rubber septum, and nitrogen inlet was charged with about 450 mL of dry THF. The flask was cooled to $-78°$ C. in a dry ice/acetone bath and 52 mL (0.52 moles) of 10M butyllithium was added via a canula. 62 mL (0.45 moles) of 2-bromo-p-xylene was added via the addition funnel to the reaction over the course of approximately 30 minutes. Then 70 mL (0.64 moles) of chlorotrimethylsilane was added over the course of 30 minutes and the reaction allowed to stir for 15 minutes. The reaction was then warmed to room temperature and the THF removed on a rotary evaporator. The crude product was then diluted with 300 mL of hexane and dried over magnesium sulfate. After removal of the solvent on a rotary evaporator the product was distilled (5.5 mm Hg/74°/79° C.) to give 69.6 g (87% yield) of 2-trimethylsily-p-xylene which was 98% pure by GC. The spectral evidence (1 H-NMR, 13C-NMR, IR, GC-MS) was consistent with the assigned structure.

EXAMPLE II

In a similar procedure as in Example I, 5-trimethylsilyl-m-xylene was prepared. The crude product was distilled (5.2 mm Hg/77° C.) to give 69.2 g (86% yield) of 5-trimethylsilyl-m-xylene which was 97% pure by gas chromatographic analysis.

EXAMPLE III

The following procedure illustrates the preparation of 1,3-bis-p-tolyl-tetramethyl disiloxane which was used as the feedstock for 1,3-bis(p-carboxyphenyl)-tetramethyl disiloxane. A 250 ml three-necked, round-bottomed flask fitted with a nitrogen gas inlet, stir bar, and rubber septa, was charged with 31.0 g (0.17 mole) p-tolyldimethylchlorosilane and 60 ml dry tetrahydrofuran (THF). Pyridine (18 ml, 0.20 mole) was introduced via syringe and the solution stored at room temperature for 30 minutes. Water (deionized, 3.62 g, 0.20 mole) was syringed into the reaction upon which it exothermed to 67° C. After 1 hour, GC analysis showed that the reaction was 80% complete. Stirring at room temperature was continued for 48 hours. The reaction mixture was filtered and solvents removed under vacuum to yield 18.7 g of 1,3-bis-(p-tolyl)-tetramethyl-disiloxane, 70 wt. % yield, 95% purity by GC.

The following batch oxidations in Examples IV-VIII by the process of the instant invention were conducted in the following manner:

Each batch oxidation was conducted by charging all of the catalyst components, the silyl reactant and acetic acid, sealing the reactor; setting a pressure control valve to 500 psig (valve was in exhaust vent line); pressuring the reactor to 500 psig with nitrogen; heating the reactor contents to the desired temperature, 150° C., and then introducing a pressurized mixture of synthetic air (20.3% O2) into the reactor at a flow rate of 0.22 SCFM. Cooling water at approximately 20° C. was introduced into the jacket of the condenser section. Temperature of the reactor was controlled via an internal cooling coil. Each oxidation was terminated when the vent gas reached a value within 1% of the synthetic air.

All oxidations were conducted initially at a gauge pressure of 500 psig, at oxidation initiation temperatures of 150° C., a weight ratio of acetic acid to silyl reactant of 20:1 and synthetic air as the source of oxygen. The oxidation reactor was a stirred 1-liter titanium cylindrical autoclave. A water-cooled condenser was placed immediately above the autoclave to condense and return a substantial portion of the volatile compounds. Following the condensation system, there were means for venting the exhaust gaseous mixture (nitrogen, unused or excess oxygen, oxides of carbon, water vapor, and vapor of uncondensed acetic acid and some of the unreacted silyl reactant) and analytical means for determining the oxygen, carbon dioxide, and carbon monoxide contents of exhaust sample on acetic acid-free dry basis. The exhaust sample flowed through a "DRIERITE" trap before analysis for $O_2$, $CO_2$ and CO. The reactor was charged with 30 grams silyl reactant and 400 grams of acetic acid for 400/30 solvent ratio to silyl reactant ratio. The temperature increased from 150°–162° C. in 40 minutes. The reactor was pressured to 500 psig with nitrogen and then heated to the initiation temperature. Thereafter pressurized synthetic air was introduced into the liquid phase in the reactor. Each oxidation was terminated when the vent oxygen reached a value within 1% of the value for the synthetic air itself, which ranged from 18 to 21% oxygen.

Reaction conditions and results are in the following examples.

EXAMPLE IV

2-Trimethylsilyl-terephthalic acid was prepared by the process of the instant invention. Yield was 81% (67% isolated).

| Reaction Conditions: | wt. (g) |
| --- | --- |
| Co(OAc)$_2$.4H$_2$O | 1.50 |
| Mn(OAc)$_2$.4H$_2$O | 1.49 |
| NaBr | 1.73 |
| HOAc | 400 |
| 2-trimethylsilyl-p-xylene | 30.00 |

Titanium autoclave, T=300°–325° F., P=500 psig, reaction time 40 mins.

EXAMPLE V

In the procedure of Example IV, 5-trimethylsilyl-isophthalic acid was prepared from the product of Example III. Yield was 92% (82% isolated).

EXAMPLE VI

In the procedure of Example IV, a siloxane diacid 1,3-bis(p-carboxyphenyl)-tetramethyl-disiloxane, was prepared from 1,3-bis-(p-tolyl) tetramethyl-disiloxane. Yield was 72% (isolated).

EXAMPLE VII

In the procedure of Example IV, 2,5-bis(trimethylsilyl)-terephthalic acid was prepared from 2,5-bis(trimethylsilyl) p-xylene.

| Amounts | |
|---|---|
| 2,5-bis(trimethylsilyl)-p-xylene | 25.7 g |
| Co(OAc)$_2$ | 1.1005 g |
| Mn(OAc)$_2$ | 1.1002 g |
| NaBr | 1.3004 g |
| HOAc | 300 g |
| Reaction Conditions | |
| Pressure | 500 psig |
| Temperature | 300–324° F. |
| Run Time | 30 minutes |

A large amount of white solids were formed. The yield of 2,5-bis(trimethylsilyl)-terephthalic acid was 41 mole %.

EXAMPLE VIII

In the procedure of Example IV, 1,2,4-tricarboxy-5-trimethylsilylbenzene was prepared from 1,2,4-trimethyl-5-trimethylsilyl-benzene.

| Amounts | |
|---|---|
| 1,2,4-trimethyl-5-trimethylsilylbenzene | 51.7 g |
| Co(OAc)$_2$ | 1.1005 g |
| Mn(OAc)$_2$ | 1.1002 g |
| NaBr | 1.3004 g |
| HOAc | 300 g |
| Reaction Conditions | |
| Pressure | 500 psig |
| Temperature | 300–324° F. |
| Run Time | 30 minutes |

The yield of 1,2,4-tricarboxy-5-trimethylsilyl-benzene was 13.5 mole %. The anhydride can be prepred by heating the tricarboxy compound in acetic anhydride to prepare 5-trimethylsilyl-1,2,4-benzenetricarboxylic anhydride.

What is claimed is:

1. A process for preparation of silicon-containing aromatic polyacids by liquid phase oxidation of a mono- or poly(mono- or polyalkyl-, aryl-, oxo-, siloxy, or silyl-substituted) silyl-substituted mono- or polyalkyl-substituted aryl compound comprising an alkyl-substituted or aryl substituted aryl mono- or polyalkyl silyl wherein alkyl groups or aryl groups in the alkyl-substituted or aryl-substituted mono- or polyalkyl silyl contain from 1 to 100 carbon atoms, the number of alkyl groups on the alkyl-substituted aryl mono- or polyalkyl silyl are from 1 to 4, the number of aryl groups in the aryl-substituted aryl-, mono- or polyalkyl silyl are from 1 to 4 and the alkyl groups in the silicon atom contain from 1 to 20 carbon atoms, which process comprises:

a) introducing into a suitable reactor a silyl compound feedstock comprising said mono- or poly(mono- or polyalkyl-, aryl-, oxo-, siloxy, or silyl-substituted) silyl- substituted mono- or polyalkyl-substituted aryl compound in a solvent acid comprising an aliphatic $C_2$ to $C_6$ monocarboxylic acid;

b) oxidizing said feedstock in the presence of a catalyst comprising cobalt-manganese-bromine with an oxygen-containing gas wherein the weight ratio of cobalt (calculated as elemental cobalt) to the said silyl compound is in the range of from about 0.2 to about 100 milligram atoms (mga) per gram mole of said silyl compound feedstock weight ratio of manganese (calculated as elemental manganese) to the cobalt of said catalyst is in the range of from about 0.2 to 100 milligram atoms (mga) per mga of cobalt, and weight ratio of bromine in said catalyst (calculated as elemental bromine) to total cobalt and manganese (calculated as elemental cobalt and manganese) is in the range of from about 0.25 to about 1.2 mga per mga of total cobalt and manganese, wherein weight ratio of said silyl compound feedstock to said aliphatic $C_2$ to $C_6$ monocarboxylic acid is from about 1:5 to about 1:10, said silyl compound feedstock to said acid, at a temperature within the range of from about 120° C. (250° F.) to about 260° C. (500° F.) and at a reaction pressure within the range of from about 50 psig to about 750 psig; and c) recovering a silicon-containing aromatic polyacid wherein said polyacid comprises a silicon-containing aromatic polyacid.

2. The process of claim 1 wherein said silyl compound feedstock is selected from the group consisting of 2-trimethylsilyl-p-xylene, 5-trimethylsilyl-m-xylene, 2,5-bis(trimethylsilyl)-p-xylene, 1,2,4-trimethyl-5-trimethylsilylbenzene, and 1,3-bis-(p-tolyl) tetramethyldisiloxane.

3. The process of claim 1 wherein said silyl compound feedstock comprises 2-trimethylsilyl-p-xylene, said $C_2$ to $C_6$ monocarboxylic acid is acetic acid, and said silicon-containing aromatic polyacid comprises 2-trimethylsilyl-terephthalic acid.

4. The process of claim 1 wherein said silyl compound feedstock comprises 5-trimethylsilyl-m-xylene, said $C_2$ to $C_6$ monocarboxylic acid is acetic acid, and said silicon-containing aromatic polyacid comprises 5-trimethylsilyl-isophthalic acid.

5. The process of claim 1 wherein said feedstock comprises 2,5-bis(trimethylsilyl)-p-xylene, said $C_2$ to $C_6$ monocarboxylic acid is acetic acid, and said silicon-containing aromatic polyacid is 2,5-bis(trimethylsilyl) terephthalic acid.

6. The process of claim 1 wherein said feedstock comprises 1,2,4-trimethyl-5-trimethylsilyl-benzene, said $C_2$ to $C_6$ monocarboxylic acid is acetic acid, and said silicon-containing aromatic acid is 1,2,4-tricarboxy-5-trimethylsilyl-benzene.

7. The process of claim 1 wherein said feedstock comprises 1,3-bis-(p-tolyl) tetramethyl-disiloxane, said $C_2$ to $C_6$ monocarboxylic acid is acetic acid, and said silicon-containing aromatic acid is 1,3-bis(p-carboxyphenyl) tetramethyl-disiloxane.

8. The process of claim 1 wherein said feedstock comprises 1-trimethylsilyl-2,6-dimethylnaphthalene, said $C_2$ to $C_6$ monocarboxylic acid is acetic acid, and said silicon-containing aromatic acid is 1-trimethylsilyl-2,6-dicarboxynaphthalene.

9. The process of claim 1 wherein said oxygen-containing gas is air.

10. The process of claim 1 wherein said process is a continuous process wherein the silyl compound feedstock is selected from the group consisting of 2-trimethylsilyl-p-xylene, 5-trimethylsilyl-m-xylene, 2,5-bis(trimethylsilyl)-p-xylene, 1,2,4-trimethyl-5-trimethylsilyl-benzene, 1,3-bis-(p-tolyl) tetramethyl-disiloxane, and 1-trimethylsilyl-2,6-dimethylnaphthalene, the $C_2$ to $C_6$ monocarboxylic acid is acetic acid, the mole ratio of manganese to cobalt is in the range of from about 0.2 to about 10.0, mole ratio of bromine to total cobalt plus manganese is about 0.2 to about 1.2, weight ratio of cobalt to said acetic acid, as glacial acetic acid, is in the range of from about 250 ppm to about 750 ppm, water content of the reaction mixture is from about 0.5 wt. % to about 2.0 wt. %, reaction temperature is in the range of from about 140° C. to about 165° C., reaction pressure is within the range of from about 200 psig to about 550 psig, wherein said oxygen-containing gas fed to said reactor provides an exhaust gas-vapor mixture containing from 0.5 to 8 volume percent oxygen, measured on a solvent-free basis and residence time is from about 30 minutes to about 6 hours.

11. A silicon-containing aromatic polyacid comprising 1,2,4-tricarboxy-5-trimethylsilyl-benzene.

12. A silicon-containing anhydride of an aromatic polyacid comprising 5-trimethylsilyl-1,2,4-benzenetricarboxylic anhydride.

* * * * *

UNITED STATES PATENT AND TRADEMARK OFFICE
CERTIFICATE OF CORRECTION

PATENT NO. : 5,082,959
DATED : January 21, 1992
INVENTOR(S) : ANDREAS B. ERNST, HOWARD B. YOKELSON & ROBERT K. GIPE It is certified that error appears in the above-identified patent and that said Letters Patent is hereby corrected as shown below:

| Col. | Line | |
|---|---|---|
| 1 | 16 | "the number of groups" should read --the number of aryl groups-- |
| 2 | 1 | "severl advantages" should read --several advantages-- |

Signed and Sealed this

First Day of June, 1993

Attest:

MICHAEL K. KIRK

Attesting Officer    Acting Commissioner of Patents and Trademarks